(12) United States Patent
Campbell et al.

(10) Patent No.: US 7,105,533 B2
(45) Date of Patent: *Sep. 12, 2006

(54) FUSED HETEROBICYCLO SUBSTITUTED PHENYL METABOTROPIC GLUTAMATE-5 MODULATORS

(75) Inventors: Brian Thomas Campbell, San Diego, CA (US); Janet Lorraine Gunzer, Berkeley, CA (US); Benito Munoz, San Diego, CA (US); Brian Andrew Stearns, San Diego, CA (US); Jean-Michel Andre Vernier, San Diego, CA (US); Bowei Wang, San Diego, CA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/527,044

(22) PCT Filed: Sep. 9, 2003

(86) PCT No.: PCT/US03/28344

§ 371 (c)(1),
(2), (4) Date: Mar. 8, 2005

(87) PCT Pub. No.: WO2004/024074

PCT Pub. Date: Mar. 25, 2004

(65) Prior Publication Data

US 2005/0240021 A1    Oct. 27, 2005

Related U.S. Application Data

(60) Provisional application No. 60/410,549, filed on Sep. 13, 2002.

(51) Int. Cl.
| | | |
|---|---|---|
| A61K 31/4375 | (2006.01) | |
| A61K 31/4439 | (2006.01) | |
| C07D 471/02 | (2006.01) | |
| C07D 487/02 | (2006.01) | |
| C07D 513/02 | (2006.01) | |

(52) U.S. Cl. ............ 514/299; 514/300; 514/338; 546/112; 546/119; 546/121; 546/268.7; 546/270.1

(58) Field of Classification Search .......... None
See application file for complete search history.

(56) References Cited

U.S. PATENT DOCUMENTS 6,124,313 A    9/2000    Grundler et al.

FOREIGN PATENT DOCUMENTS

JP         2001-35664    *    2/2001

OTHER PUBLICATIONS

Lins, Claudio L, "Nitro- para- and meta-substituted 2-phenyl-indolizines as potential antimicrobial agents," Journal of Pharmaceutical Sciences 71(5), pp. 556-561 (1982).*
Nakatsuka et al., STN International (2005) HCAPLUS Database, Accession No. 2001:98819.*
C. Lins et al., "Nitro- para- and meta-Substituted 2-Phenyl-indolizines as Potential Antimicrobial Agents", Journal of Pharmaceutical Sciences, 71(5), pp. 556-561 (1982).

* cited by examiner

Primary Examiner—Golam M. M. Shameem
Assistant Examiner—Andrew B. Freistein
(74) Attorney, Agent, or Firm—David L. Rose; David Rubin

(57) ABSTRACT

Phenyl compounds substituted with a fused-heterobicyclo moiety, are mGluR5 modulators useful in the treatment of psychiatric and mood disorders such as, for example, schizophrenia, anxiety, depression, and panic, as well as in the treatment of pain and other diseases.

12 Claims, No Drawings

FUSED HETEROBICYCLO SUBSTITUTED PHENYL METABOTROPIC GLUTAMATE-5 MODULATORS

RELATED APPLICATION DATA

This is a National filing under 35 USC 371 of PCT/US2003/028344, filed Sep. 9, 2003, which claims priority from U.S. Ser. No. 60/410,549, filed Sep. 13, 2002.

BACKGROUND OF THE INVENTION

The present invention is directed to phenyl compounds substituted with a fused-heterobicyclo moiety. In particular, this invention is directed to phenyl compounds substituted with a fused-heterobicyclo moiety which are metabotropic glutamate receptor—subtype 5 ("mGluR5") modulators useful in the treatment of psychiatric and mood disorders such as, for example, schizophrenia, anxiety, depression, and panic, as well as in the treatment of pain, Parkinson's disease; cognitive dysfunction, epilepsy, drug addiction, drug abuse, drug withdrawal and other diseases.

A major excitatory neurotransmitter in the mammalian nervous system is the glutamate molecule, which binds to neurons, thereby activating cell surface receptors. Such surface receptors are characterized as either ionotropic or metabotropic glutamate receptors. The metabotropic glutamate receptors ("mGluR") are G protein-coupled receptors that activate intracellular second messenger systems when bound to glutamate. Activation of mGluR results in a variety of cellular responses. In particular, mGluR1 and mGluR5 activate phospholipase C, which is followed by mobilizing intracellular calcium.

Modulation of metabotropic glutamate receptor subtype 5 (mGluR5) is useful in the treatment of diseases that affect the nervous system (see for example W. P. J. M Spooren et al., *Trends Pharmacol. Sci.*, 22:331–337 (2001) and references cited therein). For example, recent evidence demonstrates the involvement of mGluR5 in nociceptive processes and that modulation of mGluR5 using mGluR5-selective compounds is useful in the treatment of various pain states, including acute, persistent and chronic pain [K Walker et al., *Neuropharmacology*, 40:1–9 (2001); F. Bordi, A. Ugolini *Brain Res.*, 871:223–233 (2001)], inflammatory pain [K Walker et al., *Neuropharmacology*, 40:10–19 (2001); Bhave et al. *Nature Neurosci.* 4:417–423 (2001)] and neuropathic pain [Dogrul et al. *Neurosci. Lett.* 292:115–118 (2000)].

Further evidence supports the use of modulators of mGluR5 in the treatment of psychiatric and neurological disorders. For example, mGluR5-selective compounds such as 2-methyl-6-(phenylethynyl)-pyridine ("MPEP") are effective in animal models of mood disorders, including anxiety and depression [W. P. J. M Spooren et al., *J. Pharmacol. Exp. Ther.*, 295:1267–1275 (2000); E. Tatarczynska et al, *Brit. J. Pharmacol.*, 132:1423–1430 (2001); A. Klodzynska et al, *Pol. J. Pharmacol.*, 132:1423–1430 (2001)]. Gene expression data from humans indicate that modulation of mGluR5 may be useful for the treatment of schizophrenia [T. Ohnuma et al, *Mol. Brain. Res.*, 56:207–217 (1998); ibid, *Mol. Brain. Res.*, 85:24–31 (2000)]. Studies have also shown a role for mGluR5, and the potential utility of mGluR5-modulatory compounds, in the treatment of movement disorders such as Parkinson's disease [W. P. J. M Spooren et al., *Europ. J. Pharmacol.* 406:403–410 (2000); H. Awad et al., *J. Neurosci.* 20:7871–7879 (2000); K. Ossawa et al. *Neuropharmacol.* 41:413–420 (2001)]. Other research supports for mGluR5 modulation in the treatment of cognitive dysfunction [G. Riedel et al, *Neuropharmacol.* 39:1943–1951 (2000)], epilepsy [A. Chapman et al, *Neuropharmacol.* 39:1567–1574 (2000)] and neuroprotection [V. Bruno et al, *Neuropharmacol.* 39:2223–2230 (2000)]. Studies with mGluR5 knockout mice and MPEP also suggest that modulation of these receptors may be useful in the treatment of drug addiction, drug abuse and drug withdrawal [C. Chiamulera et al. *Nature Neurosci.* 4:873–874 (2001)].

International Patent Publications WO 01/12627 and WO 99/26927 describe heteropolycyclic compounds and their use as metabotropic glutamate receptor antagonists.

U.S. Pat. No. 3,647,809 describes pyridyl-1,2,4-oxadiazole derivatives. U.S. Pat. No. 4,022,901 describes 3-pyridyl-5-isothiocyanophenyl oxadiazoles. International Patent Publication WO 98/17652 describes oxadiazoles, WO 97/03967 describes various substituted aromatic compounds, and WO 94/22846 describes various heterocyclic compounds.

Compounds that include ringed systems are described by various investigators as effective for a variety of therapies and utilities. For example, International Patent Publication No. WO 98/25883 describes ketobenzamides as calpain inhibitors, European Patent Publication No. EP 811610 and U.S. Pat. Nos. 5,679,712, 5,693,672 and 5,747,541 describe substituted benzoylguanidine sodium channel blockers, and U.S. Pat. No. 5,736,297 describes ring systems useful as a photosensitive composition.

However, there remains a need for novel compounds and compositions that therapeutically inhibit mGluR5 with minimal side effects.

SUMMARY OF THE INVENTION

The present invention is directed to novel phenyl compounds substituted with a fused-heterobicyclo moiety, which are mGluR5 modulators useful in the treatment of psychiatric and mood disorders such as, for example, schizophrenia, anxiety, depression, and panic, as well as in the treatment of pain, Parkinson's disease, cognitive dysfunction, epilepsy, drug addiction, drug abuse, drug withdrawal and other diseases. This invention also provides a pharmaceutical composition which includes an effective amount of the phenyl compounds substituted with a fused-heterobicyclo moiety, and a pharmaceutically acceptable carrier.

This invention further provides a method of treatment of psychiatric and mood disorders such as, for example, schizophrenia, anxiety, depression, and panic, as well as a method of treatment of pain, Parkinson's disease, cognitive dysfunction, epilepsy, drug addiction, drug abuse and drug withdrawal by the administration of an effective amount of the phenyl compounds substituted with a fused-heterobicyclo moiety.

DETAILED DESCRIPTION OF THE INVENTION

The compounds of the present invention are represented by Formula (I):

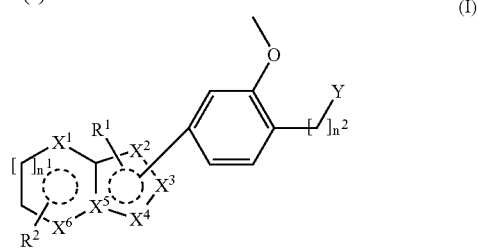

or a pharmaceutically acceptable salt thereof, wherein $X^1$, $X^2$, $X^4$, and $X^6$ are independently C, N, S or O; $X^3$ and $X^5$ are independently C or N; wherein at least one of $X^1$, $X^2$, $X^3$, $X^4$, $X^5$, and $X^6$ is N; at most one of $X^1$, $X^2$, $X^4$, and $X^6$ is S or O; Y is C0–4alkyl, aryl, or heteroaryl; $R^1$ and $R^2$ are independently halogen, C0–4alkyl, or pyridyl; and $n^1$ and $n^2$ are independently 0 or 1.

In one aspect, the compound of this invention is represented by Formula (I) or a pharmaceutically acceptable salt thereof, wherein $X^1$, $X^2$, $X^4$, and $X^6$ are independently C, N, S or O; $X^5$ is N; at most one of $X^1$, $X^2$, $X^4$, and $X^6$ is S or O; $X^3$ is C or N; Y is C0–4alkyl, aryl, or heteroaryl; $R^1$ and $R^2$ are independently halogen, C0–4alkyl, or pyridyl; and $n^1$ and $n^2$ are independently 0 or 1.

In an embodiment of this one aspect, the compound of this invention is represented by Formula (I) or a pharmaceutically acceptable salt thereof, wherein $X^1$, $X^2$, $X^3$, $X^4$, and $X^6$ are C; $X^5$ is N; Y is C0–4alkyl, aryl, or heteroaryl; $R^1$ and $R^2$ are independently halogen, C0–4alkyl, or pyridyl; and $n^1$ and $n^2$ are independently 0 or 1.

In another embodiment of this one aspect, the compound of this invention is represented by Formula (I) or a pharmaceutically acceptable salt thereof, wherein $X^1$ and $X^6$ are C; one of $X^2$, $X^3$, and $X^4$ is N, the remaining are C; $X^5$ is N; Y is C0–4alkyl, aryl, or heteroaryl; $R^1$ and $R^2$ are independently halogen, C0–4alkyl, or pyridyl; and $n^1$ and $n^2$ are independently 0 or 1.

In still another embodiment of this one aspect, the compound of this invention is represented by Formula (I) or a pharmaceutically acceptable salt thereof, wherein $X^1$ and $X^6$ are C; two of $X^2$, $X^3$, and $X^4$ are N, the remaining is C; $X^5$ is N; Y is C0–4alkyl, aryl, or heteroaryl; $R^1$ and $R^2$ are independently halogen, C0–4alkyl, or pyridyl; and $n^1$ and $n^2$ are independently 0 or 1.

In yet another embodiment of this one aspect, the compound of this invention is represented by Formula (I) or a pharmaceutically acceptable salt thereof, wherein $X^1$ is S; $X^6$ is C; one of $X^2$, $X^3$, and $X^4$ is N, the remaining are C; $X^5$ is N; Y is C0–4alkyl, aryl, or heteroaryl; $R^1$ and $R^2$ are independently halogen, C0–4alkyl, or pyridyl; and $n^1$ and $n^2$ are independently 0 or 1.

In yet still another embodiment of this one aspect, the compound of this invention is represented by Formula (I) or a pharmaceutically acceptable salt thereof, wherein $X^1$ is S; $X^6$ is N; one of $X^2$, $X^3$, and $X^4$ is N, the remaining are C; $X^5$ is N; Y is C0–4alkyl, aryl, or heteroaryl; $R^1$ and $R^2$ are independently halogen, C0–4alkyl, or pyridyl; and $n^1$ and $n^2$ are independently 0 or 1.

In a second aspect, the compound of this invention is represented by Formula (I) or a pharmaceutically acceptable salt thereof, wherein $X^1$, $X^2$, $X^4$, and $X^6$ are independently C, N, S or O; $X^5$ is C; $X^3$ is C or N; wherein at least one of $X^1$, $X^2$, $X^3$, $X^4$, $X^5$, and $X^6$ is N; at most one of $X^1$, $X^2$, $X^4$, and $X^6$ is S or O; Y is C0–4alkyl, aryl, or heteroaryl; $R^1$ and $R^2$ are independently halogen, C0–4alkyl, or pyridyl; and $n^1$ and $n^2$ are independently 0 or 1.

In an embodiment of the second aspect, the compound of this invention is represented by Formula (I) or a pharmaceutically acceptable salt thereof, wherein $X^1$ and $X^6$ are C; $X^5$ is C; Two of $X^2$, $X^3$, and $X^4$ are N, the remaining is C; Y is C0–4alkyl, aryl, or heteroaryl; $R^1$ and $R^2$ are independently halogen, C0–4alkyl, or pyridyl; and $n^1$ and $n^2$ are independently 0 or 1.

In an embodiment of the second aspect, the compound of this invention is represented by Formula (I) or a pharmaceutically acceptable salt thereof, wherein $X^1$ and $X^6$ are C; $X^5$ is C; $X^2$, $X^3$, and $X^4$ are N; Y is C0–4alkyl, aryl, or heteroaryl; $R^1$ and $R^2$ are independently halogen, C0–4alkyl, or pyridyl; and n and n are independently 0 or 1.

As used herein, "alkyl" as well as other groups having the prefix "alk" such as, for example, alkoxy, alkanoyl, alkenyl, alkynyl and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains containing at least one unsaturated C—C bond.

The term "cycloalkyl" means carbocycles containing no heteroatoms, and includes mono-, bi- and tricyclic saturated carbocycles, as well as fused ring systems. Such fused ring systems can include one ring that is partially or fully unsaturated such as a benzene ring to form fused ring systems such as benzofused carbocycles. Cycloalkyl includes such fused ring systems as spirofused ring systems. Examples of cycloalkyl include cyclopropyl, cyclobutyl, cyclopentyl, cyclohexyl, decahydronaphthalene, adamantane, indanyl, indenyl, fluorenyl, 1,2,3,4-tetrahydronaphalene and the like. Similarly, "cycloalkenyl" means carbocycles containing no heteroatoms and at least one non-aromatic C—C double bond, and include mono-, bi- and tricyclic partially saturated carbocycles, as well as benzofused cycloalkenes. Examples of cycloalkenyl include cyclohexenyl, indenyl, and the like.

The term "aryl" means an aromatic substituent which is a single ring or multiple rings fused together. When formed of multiple rings, at least one of the constituent rings is aromatic. The preferred aryl substituents are phenyl and naphthyl groups.

The term "cycloalkyloxy" unless specifically stated otherwise includes a cycloalkyl group connected by a short $C_{1-2}$alkyl length to the oxy connecting atom.

The term "$C_{0-6}$alkyl" includes alkyls containing 6, 5, 4, 3, 2, 1, or no carbon atoms. An alkyl with no carbon atoms is a hydrogen atom substituent when the alkyl is a terminal group and is a direct bond when the alkyl is a bridging group.

The term "hetero" unless specifically stated otherwise includes one or more O, S, or N atoms. For example, heterocycloalkyl and heteroaryl include ring systems that contain one or more O, S, or N atoms in the ring, including mixtures of such atoms. The hetero atoms replace ring carbon atoms. Thus, for example, a heterocyclo$C_5$alkyl is a five-member ring containing from 4 to no carbon atoms. Examples of heteroaryls include pyridinyl, quinolinyl, isoquinolinyl, pyridazinyl, pyrimidinyl, pyrazinyl, quinoxalinyl, furyl, benzofuryl, dibenzofuryl, thienyl, benzthienyl, pyrrolyl, indolyl, pyrazolyl, indazolyl, oxazolyl, benzoxazolyl, isoxazolyl, thiazolyl, benzothiazolyl, isothiazolyl, imidazolyl, benzimidazolyl, oxadiazolyl, thiadiazolyl, triazolyl, and tetrazolyl. Examples of heterocycloalkyls include azetidinyl, pyrrolidinyl, piperidinyl, piperazinyl, morpholinyl, tetrahydrofuranyl, imidazolinyl, pyrolidin-2-one, piperidin-2-one, and thiomorpholinyl.

The term "hetero$C_{0-4}$alkyl" means a heteroalkyl containing 3, 2, 1, or no carbon atoms. However, at least one heteroatom must be present. Thus, as an example, a hetero$C_{0-4}$alkyl having no carbon atoms but one N atom would be a —NH— if a bridging group and a —NH$_2$ if a terminal group. Analogous bridging or terminal groups are clear for an O or S heteroatom.

The term "amine" unless specifically stated otherwise includes primary, secondary and tertiary amines substituted with $C_{0-6}$alkyl.

The term "carbonyl" unless specifically stated otherwise includes a $C_{0-6}$alkyl substituent group when the carbonyl is terminal.

The term "halogen" includes fluorine, chlorine, bromine and iodine atoms.

The term "optionally substituted" is intended to include both substituted and unsubstituted. Thus, for example, optionally substituted aryl could represent a pentafluorophenyl or a phenyl ring. Further, optionally substituted multiple moieties such as, for example, alkylaryl are intended to mean that the aryl and the aryl groups are optionally substituted. If only one of the multiple moieties is optionally substituted then it will be specifically recited such as "an alkylaryl, the aryl optionally substituted with halogen or hydroxyl."

Compounds described herein contain one or more double bonds and may thus give rise to cis/trans isomers as well as other conformational isomers. The present invention includes all such possible isomers as well as mixtures of such isomers.

Compounds described herein can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric, and tartaric acids.

The pharmaceutical compositions of the present invention comprise a compound represented by Formula I (or pharmaceutically acceptable salts thereof) as an active ingredient, a pharmaceutically acceptable carrier and optionally other therapeutic ingredients or adjuvants. Such additional therapeutic ingredients include, for example, i) opiate agonists or antagonists, ii) calcium channel antagonists, iii) 5HT receptor agonists or antagonists iv) sodium channel antagonists, v) NMDA receptor agonists or antagonists, vi) COX-2 selective inhibitors, vii) NK1 antagonists, viii) non-steroidal anti-inflammatory drugs ("NSAID"), ix) GABA-A receptor modulators, x) dopamine agonists or antagonists, xi) selective serotonin reuptake inhibitors ("SSRI") and/or selective serotonin and norepinephrine reuptake inhibitors ("SS-NRI"), xii) tricyclic antidepressant drugs, xiv) norepinephrine modulators, xv) L-DOPA, xvi) buspirone, xvii) lithium, xviii) valproate, ixx) neurontin (gabapentin), xx) olanzapine, xxi) nicotinic agonists or antagonists including nicotine, xxii) muscarinic agonists or antagonists, xxiii) heroin substituting drugs such as methadone, levo-alpha-acetylmethadol, buprenorphine and naltrexone, and xxiv) disulfiram and acamprosate. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

Creams, ointments, jellies, solutions, or suspensions containing the compound of Formula I can be employed for topical use. Mouth washes and gargles are included within the scope of topical use for the purposes of this invention.

Dosage levels from about 0.01 mg/kg to about 140 mg/kg of body weight per day are useful in the treatment of psychiatric and mood disorders such as, for example, schizophrenia, anxiety, depression, and panic, as well as being useful in the treatment of pain which are responsive to mGluR5 inhibition, or alternatively about 0.5 mg to about 7 g per patient per day. For example, schizophrenia, anxiety, depression, and panic may be effectively treated by the administration of from about 0.01 mg to 75 mg of the compound per kilogram of body weight per day, or alternatively about 0.5 mg to about 3.5 g per patient per day. Pain may be effectively treated by the administration of from about 0.01 mg to 125 mg of the compound per kilogram of body weight per day, or alternatively about 0.5 mg to about 5.5 g per patient per day. Further, it is understood that the mGluR5 inhibiting compounds of this invention can be administered at prophylactically effective dosage levels to prevent the above-recited conditions.

The amount of active ingredient that may be combined with the carrier materials to produce a single dosage form will vary depending upon the host treated and the particular mode of administration. For example, a formulation intended for the oral administration to humans may conveniently contain from about 0.5 mg to about 5 g of active agent, compounded with an appropriate and convenient amount of carrier material which may vary from about 5 to about 95 percent of the total composition. Unit dosage forms will generally contain between from about 1 mg to about 1000 mg of the active ingredient, typically 25 mg, 50 mg, 100 mg, 200 mg, 300 mg, 400 mg, 500 mg, 600 mg, 800 mg or 1000 mg.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

In practice, the compounds represented by Formula I, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compound represented by Formula I, or pharmaceutically acceptable salts thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient. Thus, a tablet, cachet, or capsule conveniently contains 0.1 mg, 1 mg, 5 mg, 25 mg, 50 mg, 100 mg, 200 mg, 300 mg, 400 mg, or 500 mg of the active ingredient taken one or two tablets, cachets, or capsules, once, twice, or three times daily.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

The compounds and pharmaceutical compositions of this invention have been found to exhibit biological activity as mGluR5 inhibitors. Accordingly, another aspect of the invention is the treatment in mammals of, for example, schizophrenia, anxiety, depression, and panic, pain, Parkinson's disease, cognitive dysfunction, epilepsy, drug addiction, drug abuse and drug withdrawal—maladies that are amenable to amelioration through inhibition of mGluR5—by the administration of an effective amount of the compounds of this invention. The term "mammals" includes humans, as well as other animals such as, for example, dogs, cats, horses, pigs, and cattle. Accordingly, it is understood that the treatment of mammals other than humans is the treatment of clinical correlating afflictions to those above recited examples that are human afflictions.

Further, as described above, the compound of this invention can be utilized in combination with other therapeutic compounds. In particular, the combinations of the mGluR5 inhibiting compound of this invention can be advantageously used in combination with i) opiate agonists or antagonists, ii) calcium channel antagonists, iii) 5HT receptor agonists or antagonists iv) sodium channel antagonists, v) NMDA receptor agonists or antagonists, vi) COX-2 selective inhibitors, vii) NK1 antagonists, viii) non-steroidal anti-inflammatory drugs ("NSAID"), ix) GABA-A receptor modulators, x) dopamine agonists or antagonists, xi) selective serotonin reuptake inhibitors ("SSRI") and/or selective serotonin and norepinephrine reuptake inhibitors ("SSNRI"), xii) tricyclic antidepressant drugs, xiii) norepinephrine modulators, xiv) L-DOPA, xv) buspirone, xvi) lithium, xvii) valproate, xviii) neurontin (gabapentin), xix) olanzapine, xx) nicotinic agonists or antagonists including nicotine, xxi) muscarinic agonists or antagonists, xxii) heroin substituting drugs such as methadone, levo-alpha-acetylmethadol, buprenorphine and naltrexone, and xxiii) disulfiram and acamprosate.

The abbreviations used herein have the following tabulated meanings. Abbreviations not tabulated below have their meanings as commonly used unless specifically stated otherwise.

| | |
|---|---|
| Ac | acetyl |
| AIBN | 2,2'-azobis(isobutyronitrile) |
| BINAP | 1,1'-bi-2-naphthol |
| Bn | benzyl |
| CAMP | cyclic adenosine-3',5'-monophosphate |
| DAST | (diethylamino)sulfur trifluoride |
| DEAD | diethyl azodicarboxylate |
| DBU | 1,8-diazabicyclo[5.4.0]undec-7-ene |
| DIBAL | diisobutylaluminum hydride |
| DMAP | 4-(dimethylamino)pyridine |
| DMF | N,N-dimethylformamide |
| Dppf | 1,1'-bis(diphenylphosphino)-ferrocene |
| EDCI | 1-(3-dimethylaminopropyl)-3-ethylcarbodiimide hydrochloride |
| Et$_3$N | triethylamine |
| GST | glutathione transferase |
| HMDS | hexamethyldisilazide |
| LDA | lithium diisopropylamide |
| m-CPBA | metachloroperbenzoic acid |
| MMPP | monoperoxyphthalic acid |
| MPPM | monoperoxyphthalic acid, magnesium salt 6H$_2$O |
| Ms | methanesulfonyl = mesyl = SO$_2$Me |
| MsO | methanesulfonate = mesylate |
| NBS | N-bromo succinimide |
| NSAID | non-steroidal anti-inflammatory drug |

-continued

| | |
|---|---|
| o-Tol | ortho-tolyl |
| OXONE ® | 2KHSO$_5$·KHSO$_4$·K$_2$SO$_4$ |
| PCC | pyridinium chlorochromate |
| Pd$_2$(dba)$_3$ | Bis(dibenzylideneacetone) palladium(0) |
| PDC | pyridinium dichromate |
| PDE | Phosphodiesterase |
| Ph | Phenyl |
| Phe | Benzenediyl |
| PMB | para-methoxybenzyl |
| Pye | Pyridinediyl |
| r.t. | room temperature |
| Rac. | Racemic |
| SAM | aminosulfonyl or sulfonamide or SO$_2$NH$_2$ |
| SEM | 2-(trimethylsilyl)ethoxymethoxy |
| SPA | scintillation proximity assay |
| TBAF | tetra-n-butylammonium fluoride |
| Th | 2- or 3-thienyl |
| TFA | trifluoroacetic acid |
| TFAA | trifluoroacetic acid anhydride |
| THF | Tetrahydrofuran |
| Thi | Thiophenediyl |
| TLC | thin layer chromatography |
| TMS-CN | trimethylsilyl cyanide |
| TMSI | trimethylsilyl iodide |
| Tz | 1H (or 2H)-tetrazol-5-yl |
| XANTPHOS | 4,5-Bis-diphenylphosphanyl-9,9-dimethyl-9H-xanthene |
| C$_3$H$_5$ | Allyl |

| ALKYL GROUP ABBREVIATIONS | |
|---|---|
| Me = | Methyl |
| Et = | ethyl |
| n-Pr = | normal propyl |
| i-Pr = | isopropyl |
| n-Bu = | normal butyl |
| i-Bu = | isobutyl |
| s-Bu = | secondary butyl |
| t-Bu = | tertiary butyl |
| c-Pr = | cyclopropyl |
| c-Bu = | cyclobutyl |
| c-Pen = | cyclopentyl |
| c-Hex = | cyclohexyl |

Assays Demonstrating Biological Activity

The compounds of this invention were tested against the hmGluR5a receptor stably expressed in mouse fibroblast Ltk$^-$ cells (the hmGluR5a/L38-20 cell line) and activity was detected by changes in [Ca$^{++}$]$_i$, measured using the fluorescent Ca$^{++}$-sensitive dye, fura-2. InsP assays were performed in mouse fibroblast Ltk$^-$ cells (LM5a cell line) stably expressing hmGluR5a. The assays described in International Patent Publication WO 0116121 can be used.

Calcium Flux Assay

The activity of compounds was examined against the hmGluR5a receptor stably expressed in mouse fibroblast Ltk– cells (the hmGluR5a/L38 cell line). See generally Daggett et al., *Neuropharmacology* 34:871–886 (1995). Receptor activity was detected by changes in intracellular calcium ([Ca$^{2+}$]$_i$) measured using the fluorescent calcium-sensitive dye, fura-2. The hmGluR5a/L38-20 cells were plated onto 96-well plates, and loaded with 3 μM fura-2 for 1 h. Unincorporated dye was washed from the cells, and the cell plate was transferred to a 96-channel fluorimeter (SIBIA-SAIC, La Jolla, Calif.) which is integrated into a fully automated plate handling and liquid delivery system.

Cells were excited at 350 and 385 nm with a xenon source combined with optical filters. Emitted light was collected from the sample through a dichroic mirror and a 510 nm interference filter and directed into a cooled CCD camera (Princeton Instruments). Image pairs were captured approximately every Is, and ratio images were generated after background subtraction. After a basal reading of 20 s, an $EC_{80}$ concentration of glutamate (10 μM) was added to the well, and the response evaluated for another 60 s. The glutamate-evoked increase in $[Ca']_i$ in the presence of the screening compound was compared to the response of glutamate alone (the positive control).

Phosphatidylinositol Hydrolysis (PI) Assays

Inositolphosphate assays were performed as described by Berridge et al. [Berridge et al, *Biochem. J.* 206: 587–5950 (1982); and Nakajima et al., *J. Biol. Chem.* 267:2437–2442 (1992)] with slight modifications. Mouse fibroblast Ltk cells expressing hmGluR5 (hmGluR5/L38-20 cells) were seeded in 24-well plates at a density of 8×105 cells/well. One μCi of [$^3$H]-inositol (Amersham PT6–271; Arlington Heights, Ill.; specific activity=17.7 Ci/mmol) was added to each well and incubated for 16 h at 37° C. Cells were washed twice and incubated for 45 min in 0.5 mL of standard Hepes buffered saline buffer (HBS; 125 mM NaCl, 5 mM KCl, 0.62 mM $MgSO_4$, 1.8 mM $CaCl_2$, 20 mM HEPES, 6 mM glucose, pH to 7.4). The cells were washed with HBS containing 10 mM LiCl, and 400 μL buffer added to each well. Cells were incubated at 37° C. for 20 min. For testing, 50 μL of 10× compounds used in the practice of the invention (made in HBS/LiCl (100 mM)) was added and incubated for 10 minutes. Cells were activated by the addition of 10 μM glutamate, and the plates left for 1 hour at 37° C. The incubations were terminated by the addition of 1 mL ice-cold methanol to each well. In order to isolate inositol phosphates (IPs), the cells were scraped from wells, and placed in numbered glass test tubes. One mL of chloroform was added to each tube, the tubes were mixed, and the phases separated by centrifugation. IPs were separated on Dowex anion exchange columns (AG 1-X8 100–200 mesh formate form). The upper aqueous layer (750 μL) was added to the Dowex columns, and the columns eluted with 3 mL of distilled water. The eluents were discarded, and the columns were washed with 10 mLs of 60 mM ammonium formate/5 mM Borax, which was also discarded as waste. Finally, the columns were eluted with 4 mL of 800 mM ammonium formate/0.1M formic acid, and the samples collected in scintillation vials. Scintillant was added to each vial, and the vials shaken, and counted in a scintillation counter after 2 hours. Phosphatidylinositol hydrolysis in cells treated with certain exemplary compounds was compared to phosphatidylinositol hydrolysis in cells treated with the agonist alone in the absence of compound.

The compounds of this application have mGluR5 inhibitory activity as shown by values of less than 5 μM in the calcium flux assay and values of less than 100 μM in the PI assay. Preferably, the compounds should have values of less than 500 nM in the calcium flux assay and values of less than 10 μM in the PI assay. Even more preferably, the compounds should have values of less than 50 nM in the calcium flux assay and values of less than 1 μM in the PI assay Examples 1–16 have mGluR5 inhibitory activity as shown by values of less than 5 μM in the calcium flux assay and values of less than 100 μM in the PI assay.

The examples that follow are intended as an illustration of certain preferred embodiments of the invention and no limitation of the invention is implied.

Unless specifically stated otherwise, the experimental procedures were performed under the following conditions. All operations were carried out at room or ambient temperature—that is, at a temperature in the range of 18–25° C. Evaporation of solvent was carried out using a rotary evaporator under reduced pressure (600–4000 pascals: 4.5–30 mm. Hg) with a bath temperature of up to 60° C. The course of reactions was followed by thin layer chromatography (TLC) and reaction times are given for illustration only. Melting points are uncorrected and 'd' indicates decomposition. The melting points given are those obtained for the materials prepared as described. Polymorphism may result in isolation of materials with different melting points in some preparations. The structure and purity of all final products were assured by at least one of the following techniques: TLC, mass spectrometry, nuclear magnetic resonance (NMR) spectrometry or microanalytical data. When given, yields are for illustration only. When given, NMR data is in the form of delta (δ) values for major diagnostic protons, given in parts per million (ppm) relative to tetramethylsilane (TMS) as internal standard, determined at 300 MHz, 400 MHz or 500 MHz using the indicated solvent. Conventional abbreviations used for signal shape are: s. singlet; d. doublet; t. triplet; m. multiplet; br. broad; etc. In addition, "Ar" signifies an aromatic signal. Chemical symbols have their usual meanings; the following abbreviations are used: v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

METHODS OF SYNTHESIS

Compounds of the present invention can be prepared according to the following methods. The substituents are the same as in Formula I except where defined otherwise.

In accordance with another embodiment of the present invention, there are provided methods for the preparation of heteroaryl-substituted tetrazole compounds as described above. For example, many of the heterocyclic compounds described above can be prepared using synthetic chemistry techniques well known in the art (see *Comprehensive Heterocyclic Chemistry*, Katritzky, A. R. and Rees, C. W. eds., Pergamon Press, Oxford, 1984) from a heteroaryl-substituted tetrazole of Formula (I).

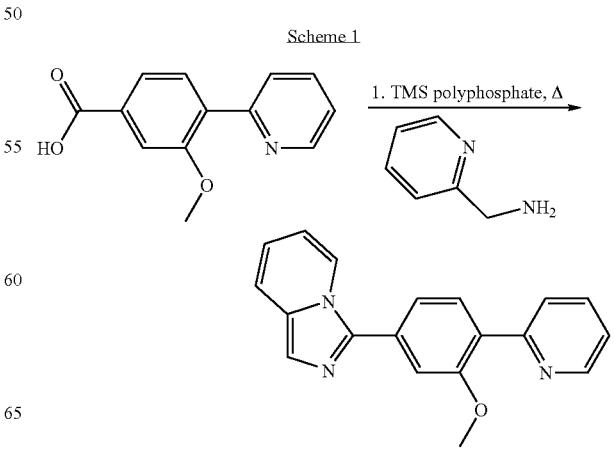

Scheme 1

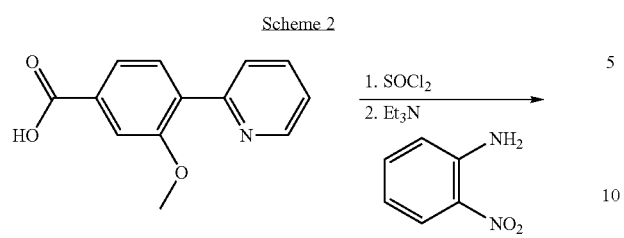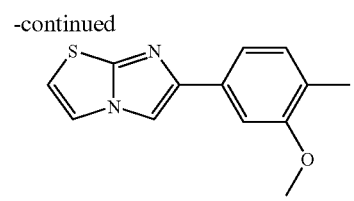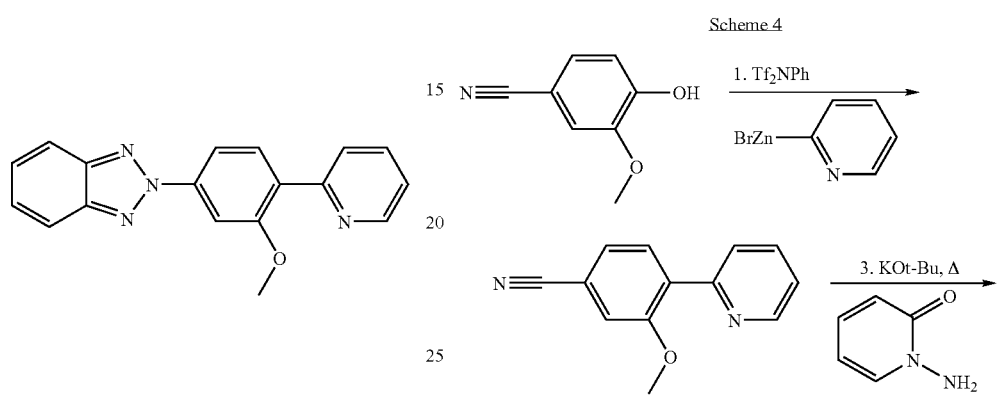

Scheme 6
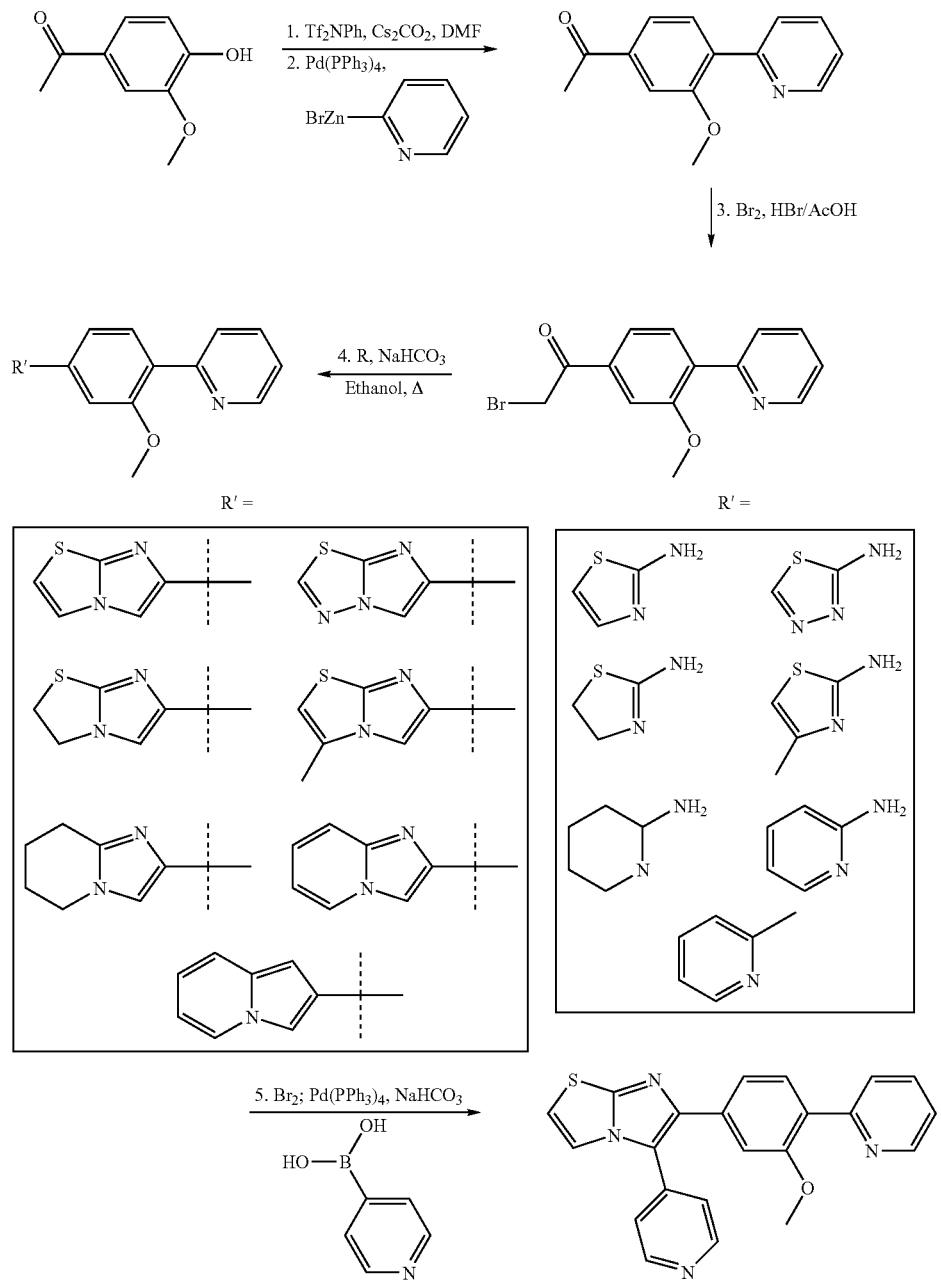
Scheme 7
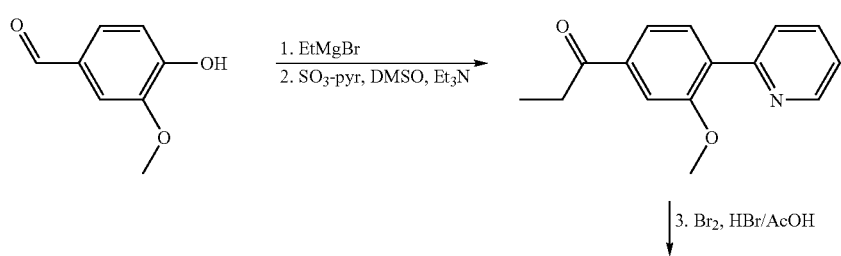

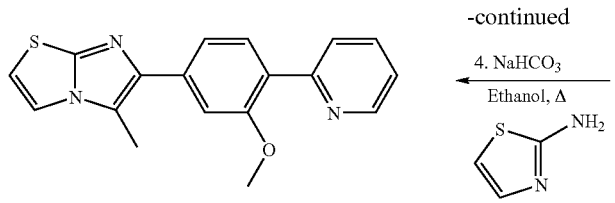

-continued

4. NaHCO₃
Ethanol, Δ

¹H NMR (DMSO-d₆, 300 MHz) δ 8.93 (d, 1H), 8.73 (d, 1H), 8.50 (t, 1H), 8.29 (s, 1H), 8.25 (d, 1H), 8.00 (d, 1H), 7.94 (m, 2H), 7.86 (s, 1H), 7.75 (d, 1H), 7.28 (dd, 1H), 7.18 (t, 1H), 4.02 (s, 3H) ppm. MS (ESI) 302 (M)⁺.

EXAMPLE 2

2-(3-methoxy-4-(pyridin-2-yl)phenyl)-2H-1,2,3-benzotriazole hydrochloride

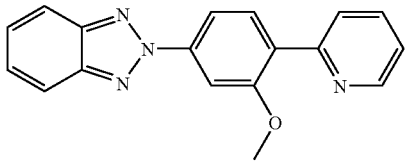

Scheme 8

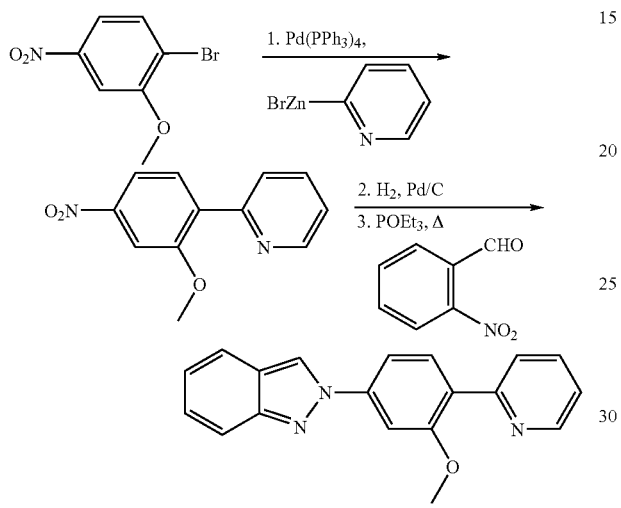

EXAMPLE 1

3-(3-methoxy-4-(pyridin-2-yl)phenyl)imidazo[1,5-a]pyridine hydrochloride

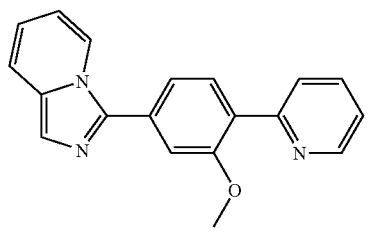

To trimethylsilylpolyphosphate (10 mL) was added 2-(aminomethyl)pyridine (0.41 mL, 4.0 mmol) and 3-methoxy-4-(pyridin-2-yl)benzoic acid (460 mg, 2.0 mmol). The mixture was heated at 200° C. for 2 h and poured over ice. The aqueous solution was made basic (pH 10) with 1N NaOH and extracted successively with tert-butyl methyl ether (1×200 mL), EtOAc (1×200 mL), CH₂Cl₂ (1×200 mL), and EtOAc (1×200 mL). The organic layers were combined, washed with brine, dried (MgSO₄), and concentrated. The crude product was purified by flash column chromatography on silica gel eluting with EtOAc:hexanes (0:1 to 1:1), the free base was taken up in ether, and HCl (1N in ether) was added to the solution. The resultant mixture was concentrated to afford desired 3-(3-methoxy-4-(pyridin-2-yl)phenyl)imidazo[1,5-a]pyridine hydrochloride as a yellow solid.

To thionyl chloride (20 mL) was added 3-methoxy-4-(pyridin-2-yl)benzoic acid (500 mg, 2.2 mmol). The mixture was heated at reflux for 3 h, cooled to rt, and concentrated. The resultant acid chloride was taken up in 20 mL of CH₂Cl₂ and the mixture cooled to 0° C. before addition of 2-nitroaniline (301 mg, 2.2 mmol) and triethylamine (0.3 mL, 2.2 mmol), and the solution warmed to rt overnight. The reaction mixture was diluted with CH₂Cl₂, washed successively with water, saturated Na₂CO₃, and brine, and the organic layer dried (MgSO₄) and concentrated. The crude product was purified by flash column chromatography on silica gel eluting with EtOAc:hexanes (1:1 to 1:1) to afford the desired 3-methoxy-4-(pyridin-2-yl)-2'-nitrobenzanilide as a yellow solid.

To toluene (1 mL) was added 3-methoxy-4-(pyridin-2-yl)-2'-nitrobenzanilide (97 mg, 0.28 mmol) and phosphorous pentachloride (56 mg, 0.27 mmol), and the mixture heated at reflux for 1 h. The resulting solution was cooled to rt and added to a solution of NaN₃ (35 mg, 0.54 mmol) in DMF (2 mL). The mixture was heated at 90° C. for 1 h, cooled to rt, partitioned between EtOAc and water, and the organic layer concentrated. The crude product was purified by flash column chromatography on silica gel eluting with EtOAc:hexanes (0:1 to 1:1) to afford 2-{2-methoxy-4-[1-(2-nitrophenyl)-1H-tetraazol-5-yl]phenyl}pyridine as a yellow solid.

2-{2-methoxy-4-[1-(2-nitrophenyl)-1H-tetraazol-5-yl]phenyl}pyridine (44 mg, 0.12 mmol) was dissolved in 1 mL of nitrobenzene, sealed in a microwave vial, and microwaved at 220° C. for 5 min. The solution was purified by flash column chromatography on silica gel eluting with EtOAc:hexanes (0:1 to 1:1), the free base was taken up in ether, and HCl (1N in ether) was added to the solution. The resultant mixture was concentrated to afford the desired 2-(3-methoxy-4-(pyridin-2-yl)phenyl)-2H-1,2,3-benzotriazole hydrochloride as a pale yellow solid.

$^1$H NMR (DMSO-$d_6$, 500 MHz) δ 8.86 (d, 1H), 8.33 (t, 1H), 8.18 (d, 1H), 8.13 (s, 1H), 8.12 (d, 1H), 8.09 (d, 1H), 8.08 (d, 1H), 8.01 (d, 1H), 7.77 (t, 1H), 7.58 (d, 1H), 7.57 (d, 1H), 4.05 (s, 3H) ppm. MS (ESI) 303 (M)$^+$.

EXAMPLE 3

2-(3-Methoxy-4-methylphenyl)imidazolo[1-2a]pyridine

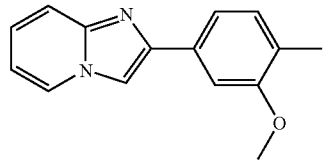

A solution of 3-methoxy-4-methyl benzoic acid (3.32 g, 20 mmol) in anhydrous THF (100 mL) was cooled to −78° C. A solution of MeLi (25 mL of a 1.6M solution in diethyl ether, 40 mmol) was added slowly to the reaction flask via syringe over 10 min. The cooling bath was removed, and the reaction mixture was allowed to warm to rt, and was stirred for 1 h at rt. The reaction mixture was quenched with 1N HCl (50 mL) and extracted with diethyl ether (3×50 mL). The organic extracts were combined, washed with brine (50 mL), dried (MgSO$_4$), and concentrated to afford 3-methoxy-4-methyl benzophenone as a colorless oil.

A solution of bromine (380 μL, 7.3 mmol) and dioxane (10 mL) was added via addition funnel over 30 min to a solution of 3-methoxy-4-methyl benzophenone (1.0 g, 6.1 mmol) and dioxane (20 mL) at rt. The reaction mixture was stirred for 30 min at rt. Triethylamine (17 mL, 12.2 mmol) and 2-aminopyridine (860 mg, 9.2 mmol) were added to the reaction, and the reaction mixture was stirred overnight. The reaction mixture was poured into water (100 mL) and was extracted with tert-butyl methyl ether (3×50 mL). The combined organic extracts were dried (MgSO$_4$) and concentrated. The crude oil was purified by flash column chromatography on silica gel eluting with EtOAc:hexanes (0:1 to 4:1) to afford the 2-(3-Methoxy-4-methylphenyl)imidazolo[1-2a]pyridine as a yellow solid. $^1$H NMR (CDCl$_3$, 300 MHz) δ 8.04 (d, 1H), 7.79 (s, 1H), 7.61 (d, 1H), 7.53 (s, 1H), 7.35 (dd, 1H), 7.16 (d, 1H), 7.11 (d, 1H), 6.72 (t, 1H), 3.94 (s, 3H), 2.26 (s, 3H) ppm. $^{13}$C NMR (CDCl$_3$, 75 MHz) 158.0, 146.0, 145.5, 132.6, 130.7, 126.4, 125.4, 124.4, 117.9, 117.3, 112.2, 107.9, 107.6, 55.4, 16.0 ppm. MS (ESI) 239 (M)$^+$.

EXAMPLE 4

2-(3-methoxy-4-pyridin-2-ylphenyl)imidazo[1,2-a]pyridine

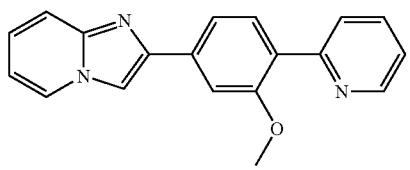

Acetovanillone (10 g, 0.06 mol), N-phenyltrifluoromethanesulfonimide (21.5 g, 0.06 mol) and cesium carbonate (19.5 g, 0.06 mol) were dissolved in acetonitrile (90 mL) and DMF (10 mL), and the solution was stirred at rt. After 12 h, the reaction mixture was diluted with diethyl ether (100 mL) and was washed successively with saturated aqueous solutions of sodium carbonate (100 mL) and brine (100 L). The organic layer was dried (MgSO$_4$), concentrated and purified by flash column chromatography on silica gel eluting with EtOAc:hexanes (1:9 to 3:7) to afford 4-acetyl-2-methoxyphenyl trifluoromethanesulfonate.

A solution of 4-acetyl-2-methoxyphenyl trifluoromethanesulfonate (5.8 g, 19.5 mmol) in THF (100 mL) was degassed by bubbling argon through the solution for 15 min, then treated with 2-pyridylzinc bromide (39 mL of 0.5M in THF, 19.5 mmol) and Pd(PPh$_3$)$_4$ (1.1 g, 0.97 mmol). The resulting reaction mixture was degassed again and heated to reflux for 12 h under an atmosphere of argon. The reaction mixture was cooled to rt, concentrated and purified by flash column chromatography on silica gel eluting with EtOAc:hexanes (1:9 to 2:3) to afford 1-(3-methoxy-4-pyridin-2-ylphenyl)ethanone.

A solution of 1-(3-methoxy-4-pyridin-2-ylphenyl)ethanone (400 mg, 1.7 mmol) in benzene (6 mL) and 30% HBr/Acetic acid (6 mL) was cooled to 0° C. and was treated with a solution of bromine (0.086 mL, 1.67 mmol) in benzene (1 mL) over 1 h. The reaction was stirred for an additional 30 min, then poured into an iced solution of saturated aqueous NaHCO$_3$ (100 mL), and the product was extracted into ethyl acetate (3×50 mL). The combined organic layers were dried (MgSO$_4$) and concentrated to afford 2-bromo-1-(3-methoxy-4-pyridin-2-ylphenyl)ethanone.

To a solution of 2-bromo-1-(3-methoxy-4-pyridin-2-ylphenyl)ethanone (130 mg, 0.42 mmol) in ethanol (5 mL) was added 2-aminopyridine (40 mg, 0.42 mmol). The resulting reaction mixture was heated to reflux for 2 h and concentrated. The residue was dissolved in CH$_2$Cl$_2$ (20 mL) and washed with a solution of saturated aqueous NaHCO$_3$ (3×10 mL), dried (MgSO$_4$) and concentrated. The residue was purified by flash column chromatography on silica gel eluting with EtOAc:hexanes (1:1 to 1:0) to afford 2-(3-methoxy-4-pyridin-2-ylphenyl)imidazo[1,2-a]pyridine as a yellow solid. $^1$H NMR (CDCl$_3$, 300 MHz) δ 8.72 (d, 1H), 8.13 (d, 1H), 7.75 (s, 1H), 7.91 (d, 1H), 7.87 (d, 1H), 7.75 (s, 1H), 7.70 (dd, 1H), 7.66 (d, 1H), 7.57 (dd, 1H), 7.20 (m, 2H), 6.79 (dd, 1H), 4.00 (s, 3H) ppm. MS (ESI) 302 (M)$^+$.

EXAMPLE 5

2-(3-methoxy-4-pyridin-2-ylphenyl)-5,6,7,8-tetrahydroimidazo[1,2-a]pyridine

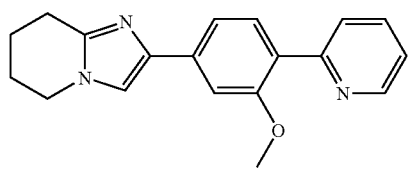

A solution of 2-(3-methoxy-4-pyridin-2-ylphenyl)imidazo[1,2-a]pyridine (40 mg, 0.13 mmol) in methanol (2 mL) was treated with Pd/C (8 mg of 10%) and stirred vigorously under an atmosphere of hydrogen gas for 3 days. The reaction mixture was filtered through a pad of celite, and the filtrate was concentrated to afford the desired 2-(3-methoxy- 4-pyridin-2-ylphenyl)-5,6,7,8-tetrahydroimidazo[1,2-a]pyridine as a yellow solid. ¹H NMR (CD₃OD, 300 MHz) δ 8.88 (d, 1H), 8.69 (m, 1H), 8.35 (d, 1H), 8.09 (m, 2H), 7.86 (m, 1H), 7.70 (s, 1H), 7.60 (d, 1H), 4.28 (br s, 2H), 4.09 (s, 3H), 3.17 (br s, 2H), 2.15 (br s, 4H) ppm. MS (ESI) 306 (M)⁺.

EXAMPLE 6

2-(3-methoxy-4-pyridin-2-ylphenyl)indolizine

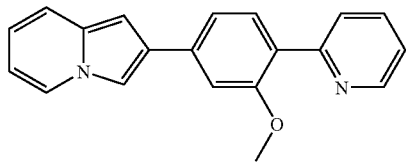

A solution of 2-bromo-1-(3-methoxy-4-pyridin-2-ylphenyl)ethanone (0.44 mmol) and 2-picoline (41 mg, 0.44 mmol) in acetone (2 mL) was heated to reflux for 3 h, diluted with CH₂Cl₂ (20 mL) and water (10 mL). The aqueous layer was separated and extracted with CH₂Cl₂ (2×10 mL), and the combined organic layers were dried (MgSO₄) and concentrated. The residue was purified by flash column chromatography on silica gel eluting with EtOAc:hexanes (1:19 to 1:2) to afford 2-(3-methoxy-4-pyridin-2-ylphenyl)indolizine. ¹H NMR (CDCl₃, 300 MHz) δ 8.75 (m, 1H), 7.92 (m, 2H), 7.86 (d, 1H), 7.73 (dt, 1H), 7.65 (br s, 1H), 7.41 (dd, 1H), 7.38 (d, 1H), 7.30 (br s, 1H), 7.21 (m, 1H), 6.77 (s, 1H), 6.69 (dd, 1H), 6.49 (dt, 1H), 3.97 (s, 3H) ppm. ¹³C NMR (CDCl₃, 75 MHz) δ 157.3, 156.0, 149.4, 137.3, 135.7, 133.7, 131.5, 129.1, 127.2, 125.1, 125.1, 121.6, 119.1, 119.1, 117.6, 110.8, 109.6, 109.2, 96.8, 55.7 ppm. MS (ESI) 301 (M)⁺.

EXAMPLE 7

2-(3-methoxy-4-pyridin-2-ylphenyl)-2H-indazole

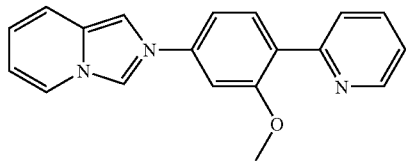

A solution of 2-bromo-5-nitroanisole (5.8 g, 25 mmol) in THF (50 mL) was treated with 2-pyridyl-zinc bromide (50 mL of a 0.5M solution in THF, 25 mmol) and Pd(PPh₃)₄ (1.44 g, 1.25 mmol). The reaction mixture was degassed by bubbling argon through the solution for min and was subsequently heated to reflux for 12 h while under an atmosphere of argon. The cooled reaction mixture was concentrated and purified by flash column chromatography on silica gel eluting with EtOAc:hexanes (1:19 to 2:3) to afford the desired 2-(2-methoxy-4-nitrophenyl)pyridine.

A suspension of Pd/C (0.25 g of 10%) in MeOH (5 mL) was mixed with a solution of 2-(2-methoxy-4-nitrophenyl) pyridine (0.5 g, 2.17 mmol) in MeOH (5 mL). The resulting reaction mixture was stirred vigorously for 12 h under an atmosphere of hydrogen, filtered through a pad of celite, and the filtrate was concentrated and purified by flash column chromatography on silica gel with EtOAc:hexanes (1:9 to 3:2) to afford 3-methoxy-4-pyridin-2-ylaniline.

A solution of 3-methoxy-4-pyridin-2-ylaniline (130 mg, 0.65 mmol) and 2-nitrobenzaldehyde (100 mg, 0.65 mmol) in toluene (1 mL) was heated to 60° C. for 12 h and the reaction mixture was concentrated to afford 3-methoxy-N-[2-nitrophenyl)methylidene]-4-pyridin-2-ylaniline. The 3-methoxy-N-[2-nitrophenyl)methylidene]-4-pyridin-2-ylaniline was dissolved in freshly distilled triethylphosphite (1.1 mL) and was heated to 110° C. for 5 h under an atmosphere of nitrogen. The reaction was cooled to 60° C. and the triethylphosphite was distilled off leaving a residue which was purified by flash column chromatography on silica gel eluting with EtOAc:hexanes (1:9 to 3:2) to afford the desired 2-(3-methoxy-4-pyridin-2-ylphenyl)-2H-indazole. ¹H NMR (CDCl₃, 500 MHz) δ 8.74 (m, 1H), 8.50 (s, 1H), 7.99 (d, 1H), 7.92 (dt, 1H), 7.83 (d, 1H), 7.75 (m, 3H), 7.52 (dd, 1H), 7.36 (ddd, 1H), 7.25, ddd, 1H), 7.14 (dd, 1H), 4.05 (s, 3H) ppm. ¹³C NMR (CDCl₃, 125 MHz) δ 157.9, 154.9, 149.7, 149.5, 141.6, 135.7, 132.0, 128.4, 127.0, 125.1, 122.8, 122.5, 121.9, 120.6, 120.4, 117.8, 112.4, 104.7, 56.0 ppm. MS (ESI) 302 (M)⁺.

EXAMPLE 8

2-(3-methoxy-4-pyridin-2-ylphenyl)pyrazolo[1,5-a]pyridine

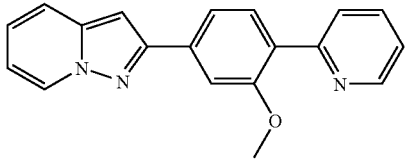

The 4-hydroxy-3-methylbenzonitrile (5 g, 33.5 mmol), N-phenyltrifluoromethanesulfonimide (12.0 g, 33.5 mmol) and cesium carbonate (10.9 g, 33.5 mmol) were dissolved in acetonitrile (50 mL) and DMF (5 mL), and the solution was stirred at rt. After 12 h, the reaction mixture was diluted with diethyl ether (100 mL) and was washed successively with saturated aqueous solutions of sodium carbonate (2×100 mL) and brine (100 mL). The organic layer was dried (MgSO₄) and concentrated to afford 4-cyano-2-methoxyphenyl trifluoromethanesulfonate.

A solution of 2-(tributylstannyl)pyridine (18 g of 80% pure, 39.2 mmol) and 4-cyano-2-methoxyphenyl trifluoromethanesulfonate (9.2 g, 32.7 mmol) were dissolved in DMF (65 mL) and treated with lithium chloride (1.39 g, 32.7 mmol) and Pd(PPh₃)₄ (1.9 g, 1.6 mmol), then degassed by bubbling argon through the solution for 15 min. The reaction mixture was heated to 100° C. while under an atmosphere of argon for 12 h. The cooled reaction mixture was diluted with diethyl ether (100 mL) and water (100 mL). The organic layer was separated and washed with a 1M solution of sodium hydroxide (50 mL) and brine (50 mL), then dried (MgSO₄) and concentrated. The residue was purified by flash column chromatography on silica gel eluting with EtOAc:hexanes (1:9 to 1:1) to afford 3-methyoxy-4-pyridin-2-ylbenzonitrile.

A solution of 3-methyoxy-4-pyridin-2-ylbenzonitrile (600 mg, 2.64 mmol) in CH₂Cl₂ (10 mL) was cooled to −78° C. and was treated with diisobutylalumnium hydride (3.2 mL of 1M in CH₂Cl₂, 3.2 mmol). After stirring the reaction mixture at −78° C. for 2 h, the temperature was raised to −40° C. before quenching the reaction with a mixture of silica gel (6 g) and water (2 mL) and then warmed to rt. The reaction mixture was dried (K₂CO₃ and MgSO₄), and concentrated. The residue was purified by flash column chromatography on silica gel eluting with EtOAc:hexanes (1:4 to 1:1) to afford 3-methoxy-4-pyridin-2-ylbenzaldehyde.

Ethyl(triphenylphosphoranylidene)acetate (550 mg, 1.6 mmol) and 3-methoxy-4-pyridin-2-ylbenzaldehyde (225 mg, 1.1 mmol) were dissolved in CH₂Cl₂ (5 mL) and stirred at rt for 12 h. The reaction mixture was concentrated and purified by flash column chromatography on silica gel eluting with EtOAc:hexanes (1:9 to 2:3) to afford the desired ethyl(2E)-3-(3-methoxy-4-pyridin-2-ylphenyl)prop-2-enoate.

A solution of ethyl(2E)-3-(3-methoxy-4-pyridin-2-ylphenyl)prop-2-enoate (55 mg, 0.2 mmol) and 1-aminopyridinium iodide (86 mg, 0.4 mmol) in DMF (1 mL) was stirred at rt for 2 days open to the atmosphere. The deep purple reaction mixture was diluted with CH₂Cl₂ (25 mL) and washed with a saturated solution of sodium thiosulfate (25 mL) and brine (25 mL), then dried (MgSO₄) and concentrated. The residue was purified by flash column chromatography on silica gel eluting with EtOAc:hexanes (1:9 to 3:2) to afford the desired ethyl 2-(3-methoxy-4-pyridin-2-ylphenyl)pyrazolo[1,5-a]pyridin-3-carboxylate as a white solid.

Ethyl 2-(3-methoxy-4-pyridin-2-ylphenyl)pyrazolo[1,5-a]pyridin-3-carboxylate (25 mg, 0.013 mmol) was treated with 40% sulfuric acid (1 mL), and the reaction mixture was heated to 100° C. for 12 h. The cooled reaction mixture was diluted with a solution of saturated aqueous sodium carbonate (25 mL), and the product was extracted into CH₂Cl₂ (3×20 mL), dried (MgSO₄) and concentrated to afford 2-(3-methoxy-4-pyridin-2-ylphenyl)pyrazolo[1,5-a]pyridine.

¹H NMR (CDCl₃, 500 MHz) δ 8.75 (d, 1H), 8.52 (d, 1H), 7.93 (d, 1H), 7.91 (d, 1H), 7.75 (dt, 1H), 7.72 (s, 1H), 7.66 (d, 1H), 7.56 (d, 1H), 7.24 (m, 1H), 7.14 (dd, 1H), 6.89 (s, 1H), 6.79 (t, 1H), 4.01 (s, 3H) ppm. MS (ESI) 302 (M)⁺.

EXAMPLE 9

2-(3-methoxy-4-pyridin-2-ylphenyl)[1,2,4]triazolo[1,5-a]pyridine

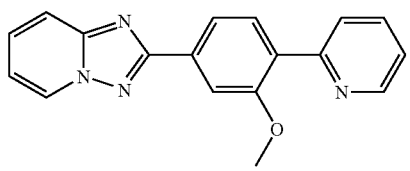

3-methyoxy-4-pyridin-2-ylbenzonitrile (104 mg, 0.95 mmol) and 1-aminopyridin-2(1H)-one (198 mg, 0.95 mmol) were dissolved in a solution of potassium t-butoxide (2 mL of 1M in t-butanol, 2.0 mmol). The reaction mixture was heated to 115° C. for 1 h, cooled and concentrated. The residue was purified by flash column chromatography on silica gel eluting with MeOH:CH₂Cl₂ (1:19) to afford the desired 2-(3-methoxy-4-pyridin-2-ylphenyl)[1,2,4]triazolo[1,5-a]pyridine. ¹H NMR (CDCl₃, 300 MHz) δ 8.75 (m, 1H), 8.64 (d, 1H), 8.06 (dd, 1H), 7.97 (s, 1H), 7.94 (m, 2H), 7.81 (d, 1H), 7.74 (dt, 1H), 7.55 (m, 1H), 7.25 (m, 1H), 7.05 (dt, 1H), 4.03 (s, 3H) ppm. ³C NMR (CDCl₃, 75 MHz) δ 163.8, 157.2, 155.5, 151.7, 149.4, 135.7, 132.2, 131.5, 130.6, 129.6, 128.3, 125.2, 121.9, 120.0, 116.4, 113.8, 110.0, 55.8 ppm. MS (ESI) 303 (M)⁺.

EXAMPLE 10

6-(3-methoxy-4-pyridin-2-ylphenyl)imidazo[2,1-b][1,3]thiazole

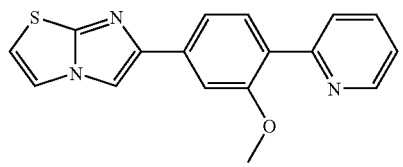

A solution of 2-bromo-1-(3-methoxy-4-pyridin-2-ylphenyl)ethanone (520 mg, 1.7 mmol) and 2-aminothiazole (170 mg, 1.7 mmol) in ethanol (10 mL) was heated to reflux for 12 h, then concentrated. The residue was dissolved in ethyl acetate (25 mL) and washed with a solution of saturated aqueous sodium bicarbonate (25 mL), then dried (MgSO₄) and concentrated. The residue was purified by flash column chromatography on silica gel eluting with EtOAc to MeOH:EtOAc (1:19) to afford 6-(3-methoxy-4-pyridin-2-ylphenyl)imidazo[2,1-b][1,3]thiazole.

¹H NMR (CDCl₃, 500 MHz) δ 8.73 (m, 1H), 7.92 (d, 1H), 7.89 (d, 1H), 7.86 (s, 1H), 7.73 (dt, 1H), 7.64 (s, 1H), 7.48 (s, 1H), 7.46 (d, 1H), 7.22 (m, 1H), 6.87 (d, 1H), 4.04 (s, 3H) ppm. MS (ESI) 308 (M)⁺.

EXAMPLE 11

6-(3-methoxy-4-pyridin-2-ylphenyl)-2,3-dihydroimidazo[2,1-b][1,3]thiazole

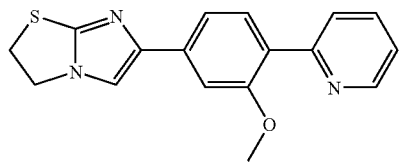

A solution of 2-bromo-1-(3-methoxy-4-pyridin-2-ylphenyl)ethanone (200 mg, 0.65 mmol) and 2-amino-2-thiazoline (67 mg, 0.65 mmol) in ethanol (5 mL) was heated to reflux for 2 h, then concentrated. The residue was dissolved in ethyl acetate (25 mL) and washed with a solution of saturated aqueous sodium bicarbonate (10 mL) and brine (10 mL), then dried (MgSO₄) and concentrated. The residue was purified by flash column chromatography on silica gel eluting with EtOAc:hexanes (2:1) to afford 6-(3-methoxy-4-pyridin-2-ylphenyl)-2,3-dihydroimidazo[2,1-b][1,3]thiazole. ¹H NMR (CD₃OD, 300 MHz) δ 8.86 (d, 1H), 8.67 (t, 1H), 8.35 (d, 1H), 8.17 (s, 1H), 8.04 (m, 1H), 7.84 (m, 1H), 7.62 (s, 1H), 7.54 (m, 1H), 4.60 (m, 2H), 4.26 (m, 2H), 4.07 (s, 3H) ppm. MS (ESI) 310 (M)⁺.

EXAMPLE 12

6-(3-methoxy-4-pyridin-2-ylphenyl)-3-methylimidazo[2,1-b][1,3]thiazole

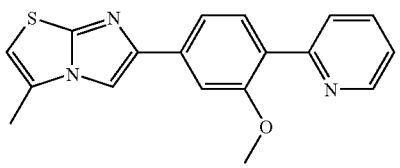

A solution of 2-bromo-1-(3-methoxy-4-pyridin-2-ylphenyl)ethanone (300 mg, 0.98 mmol) and 2-amino-4-methylthiazole (112 mg, 0.98 mmol) in ethanol (5 mL) was heated to reflux for 2 h, then concentrated. The residue was dissolved in ethyl acetate (25 mL) and washed with a solution of saturated aqueous sodium bicarbonate (10 mL) and brine (10 mL), then dried (MgSO$_4$) and concentrated. The residue was purified by flash column chromatography on silica gel eluting with EtOAc:hexanes (2:1) to afford 6-(3-methoxy-4-pyridin-2-ylphenyl)-3-methylimidazo[2,1-b][1,3]thiazole. $^1$H NMR (CD$_3$OD, 500 MHz) δ 8.91 (d, 1H), 8.85 (s, 1H), 8.74 (t, 1H), 8.47 (d, 1H), 8.11 (t, 1H), 7.94 (d, 1H), 7.78 (s, 1H), 7.73 (d, 1H), 7.33 (s, 1H), 4.13 (s, 3H), 2.68 (s, 3H) ppm. MS (ESI) 322 (M)$^+$.

EXAMPLE 13

6-(3-methoxy-4-pyridin-2-ylphenyl)-5-methylimidazo[2,1-b][1,3]thiazole

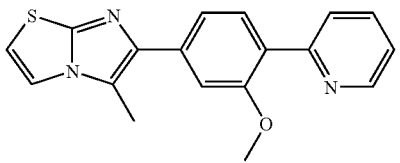

A solution of 3-methoxy-4-pyridin-2-ylbenzaldehyde (150 mg, 0.7 mmol) in THF (3 mL) was cooled to 0° C. and was treated with ethyl magnesium bromide (0.9 mL of a 1M solution in THF, 0.9 mmol). The reaction mixture was kept at 0° C. for 2 h before quenching with water (5 mL). The product was extracted into CH$_2$Cl$_2$ (3×10 mL), dried (MgSO$_4$) and concentrated. The residue was purified by flash column chromatography on silica gel eluting with EtOAc:hexanes (1:4 to 1:1) to afford 1-(3-methoxy-4-pyridin-2-ylphenyl)propan-1-ol.

A solution of 1-(3-methoxy-4-pyridin-2-ylphenyl)propan-1-ol (134 mg, 0.55 mmol) was dissolved in CH$_2$Cl$_2$ (3 mL), DMSO (0.5 mL), Et$_3$N (0.5 mL) and was treated with sulfur trioxide pyridine complex (350 mg, 2.2 mmol) at 0° C. for 12 h. The reaction mixture was diluted with water (10 mL) and the product was extracted into CH$_2$Cl$_2$ (3×10 mL), dried (MgSO$_4$), concentrated and purified by flash column chromatography on silica gel eluting with EtOAc:hexanes (1:9 to 1:1) to afford 1-(3-methoxy-4-pyridin-2-ylphenyl)propan-1-one.

A solution of 1-(3-methoxy-4-pyridin-2-ylphenyl)propan-1-one (120 mg, 0.5 mmol) in benzene (1 mL) and 30% HBr/Acetic acid (1 mL) was cooled to 0° C. and was treated with a solution of bromine (0.024 mL, 0.5 mmol) in benzene (0.5 mL) over 1 h. The reaction was stirred for an additional 30 min, then poured into an iced solution of saturated aqueous NaHCO$_3$ (100 mL), and the product was extracted into ethyl acetate (3×50 mL). The combined organic layers were dried (MgSO$_4$) and concentrated to afford 2-bromo-1-(3-methoxy-4-pyridin-2-ylphenyl)propan-1-one.

A solution of 2-bromo-1-(3-methoxy-4-pyridin-2-ylphenyl)propan-1-one (153 mg, 0.50 mmol) and 2-aminothiazole (50 mg, 0.50 mmol) in ethanol (1 mL) was heated to reflux for 12 h, then concentrated. The residue was dissolved in ethyl acetate (25 mL) and washed with saturated aqueous NaHCO$_3$ (10 mL) and brine (10 mL). The organic layer was dried (MgSO$_4$), concentrated and purified by flash column chromatography on silica gel eluting with EtOAc:hexanes (2:1 to 1:0) to afford 6-(3-methoxy-4-pyridin-2-ylphenyl)-5-methylimidazo[2,1-b][1,3]thiazole. $^1$H NMR (CDCl$_3$, 500 MHz) δ 8.73 (m, 1H), 7.94 (d, 1H), 7.88 (d, 1H), 7.73 (dt, 1H), 7.52 (s, 1H), 7.35 (dd, 1H), 7.34 (dd, 1H), 7.22 (m, 1H), 6.86 (dd, 1H), 3.98 (s, 3H), 2.66 (s, 3H) ppm. MS (ESI) 322 (M)$^+$.

EXAMPLE 14

5-bromo-6-(3-methoxy-4-pyridin-2-ylphenyl)imidazo[2,1-b][1,3]thiazole

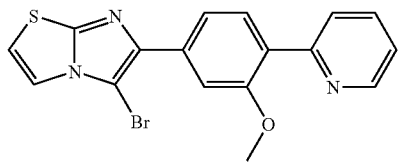

A solution of 6-(3-methoxy-4-pyridin-2-ylphenyl)-imidazo[2,1-b][1,3]thiazole (100 mg, 0.33 mmol) in CH$_2$Cl$_2$ (3 mL) was treated with a solution of bromine (0.017 mL, 0.33 mmol) in CH$_2$Cl$_2$ (1 mL) over 1 h at 0° C. The reaction mixture was diluted with CH$_2$Cl$_2$ (25 mL) and was washed with a solution of saturated aqueous sodium bicarbonate (25 mL). The organic layer was dried (MgSO$_4$) and concentrated to afford 5-bromo-6-(3-methoxy-4-pyridin-2-ylphenyl)imidazo[2,1-b][1,3]thiazole. $^1$H NMR (CD$_3$OD, 500 MHz) δ 7.29 (d, 1H), 7.12 (dt, 1H), 6.82 (d, 1H), 6.47 (dd, 1H), 6.36 (s, 1H), 6.35 (dd, 1H), 6.27 (m, 2H), 5.83 (d, 1H), 2.49 (s, 3H) ppm. MS (ESI) 388 (M)$^+$.

EXAMPLE 15

6-(3-methoxy-4-pyridin-2-ylphenyl)-5-pyridin-4-ylimidazo[2,1-b][1,3]thiazole

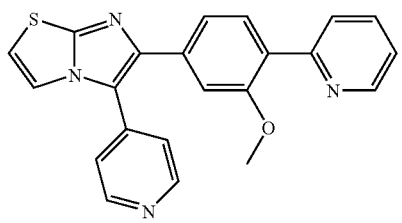

A solution of 5-bromo-6-(3-methoxy-4-pyridin-2-ylphenyl)imidazo[2,1-b][1,3]thiazole in toluene (1 mL), ethanol (0.5 mL) and a saturated solution of NaHCO$_3$ (0.5 mL), was degassed by bubbling nitrogen through the solution for 15 min. The solution was treated with Pd(PPh$_3$)$_4$ (6 mg, 0.005 mmol), degassed again and heated to 90° C. under an atmosphere of nitrogen overnight. The cooled reaction mixture was diluted with CH$_2$Cl$_2$ (10 mL) and water (10 mL). The organic layer was separated, washed with brine, dried (MgSO$_4$), and concentrated. The residue was purified by flashed column chromatography on silica gel eluting with EtOAc:hexanes (1:1 to 1:0) to afford 6-(3-methoxy-4-pyridin-2-ylphenyl)-5-pyridin-4-ylimidazo[2,1-b][1,3]thiazole. $^1$H NMR (CDCl$_3$, 500 MHz) δ 8.71 (m, 3H), 7.88 (d, 1H), 7.73 (m, 2H), 7.55 (d, 1H), 7.43 (dt, 2H), 7.37 (d, 1H), 7.22 (m, 2H), 6.96 (d, 1H), 3.83 (s, 3H) ppm. MS (ESI) 385 (M)$^+$.

EXAMPLE 16

6-(3-methoxy-4-pyridin-2-ylphenyl)imidazo[2,1-b][1,3,4]thiadiazole

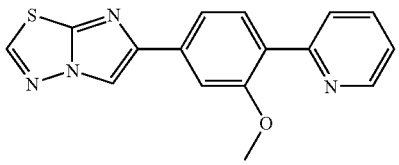

A solution of 2-bromo-1-(3-methoxy-4-pyridin-2-ylphenyl)ethanone (150 mg, 0.49 mmol) and 2-amino-1,3,4-thiadiazole (49 mg, 0.49 mmol) in ethanol (3 mL) was heated to reflux for 2 h, then concentrated. The residue was dissolved in ethyl acetate (25 mL) and washed with saturated aqueous NaHCO$_3$ (10 mL), brine (10 mL), dried (MgSO$_4$), and concentrated. The residue was purified by flash column chromatography on silica gel eluting with EtOAc:hexanes (2:1) to afford 6-(3-methoxy-4-pyridin-2-ylphenyl)imidazo[2,1-b][1,3,4]thiadiazole. $^1$H NMR (CD$_3$OD, 300 MHz) δ 9.28 (s, 1H), 8.91 (s, 1H), 8.84 (d, 1H), 8.68 (dt, 1H), 8.37 (d, 1H), 8.05 (ddd, 1H), 7.85 (d, 1H), 7.81 (br s, 1H), 7.72 (dd, 1H), 4.09 (s, 3H) ppm. MS (ESI) 309 (M)$^+$.

Other variations or modifications, which will be obvious to those skilled in the art, are within the scope and teachings of this invention. This invention is not to be limited except as set forth in the following claims.

What is claimed is:

1. A compound represented by Formula (I):

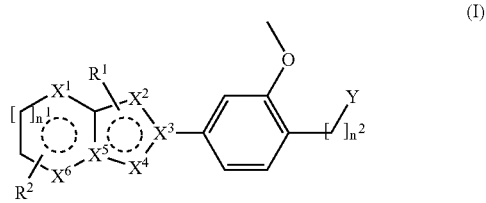

or a pharmaceutically acceptable salt thereof, wherein $X^1$, $X^2$, $X^4$, and $X^6$ are independently C, N, S or O; $X^3$ is C; and $X^5$ is N; wherein at most one of $X^1$, $X^2$, $X^4$, and $X^6$ is S or O; Y is heteroaryl; $R^1$ and $R^2$ are independently halogen, $C_{0-4}$alkyl, or pyridyl; and $n^1$ and $n^2$ are independently 0 or 1.

2. The compound according to claim 1, or a pharmaceutically acceptable salt thereof, wherein $X^1$, $X^2$, $X^3$, $X^4$, and $X^6$ are C.

3. The compound according to claim 1, or a pharmaceutically acceptable salt thereof, wherein one of $X^2$ and $X^4$ is N, the other is C; and $X^1$ and $X^6$ are C.

4. The compound according to claim 1, or a pharmaceutically acceptable salt thereof, wherein $X^2$ and $X^4$ are N, and $X^1$ and $X^6$ are C.

5. The compound according to claim 1, or a pharmaceutically acceptable salt thereof, wherein one of $X^2$ and $X^4$ is N, the other is C; $X^1$ is S; and $X^6$ is C.

6. The compound according to claim 1, or a pharmaceutically acceptable salt thereof, wherein one of $X^2$ and $X^4$ is N, the other is C; $X^1$ is S; and $X^6$ is N.

7. A compound represented by

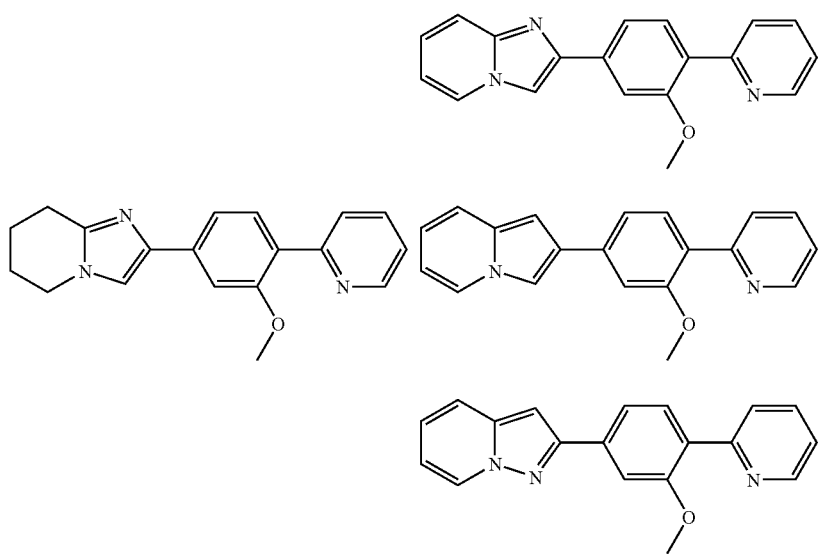

-continued

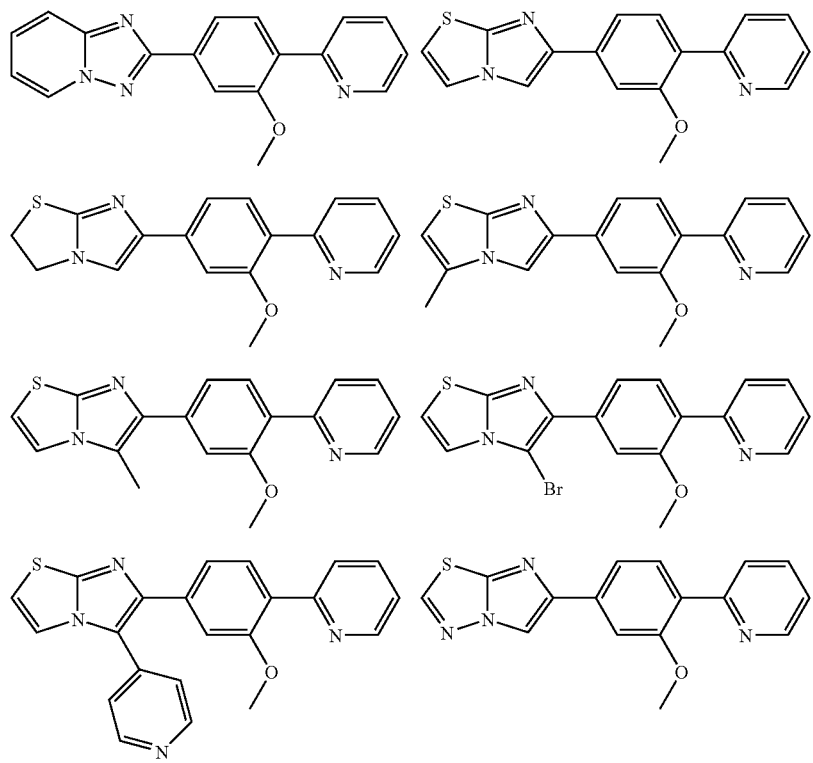

or a pharmaceutically acceptable salt thereof.

8. A pharmaceutical composition comprising: a therapeutically effective amount of the compound according to claim 1, or a pharmaceutically acceptable salt thereof; and a pharmaceutically acceptable carrier.

9. A method of treatment of pain comprising the step of administering a therapeutically effective amount of the compound according to claim 1 or a pharmaceutically acceptable salt thereof.

10. A method of treatment of a pain disorder wherein said pain disorder is acute pain, persistent pain, chronic pain, inflammatory pain, or neuropathic pain, comprising the step of administering a therapeutically effective amount of the compound according to claim 1 or a pharmaceutically acceptable salt thereof.

11. A method of treatment of neuropathic pain comprising the step of administering a therapeutically effective amount of the compound according to claim 1 or a pharmaceutically acceptable salt thereof.

12. A method of treatment of inflammatory pain comprising the step of administering a therapeutically effective amount of the compound according to claim 1 or a pharmaceutically acceptable salt thereof.

* * * * *